(12) United States Patent
Farin

(10) Patent No.: US 9,078,769 B2
(45) Date of Patent: Jul. 14, 2015

(54) SPINE SURGERY DEVICE

(76) Inventor: Azadeh Farin, Rolling Hills, CA (US)

( * ) Notice: Subject to any disclaimer, the term of this patent is extended or adjusted under 35 U.S.C. 154(b) by 205 days.

(21) Appl. No.: 13/576,767

(22) PCT Filed: Feb. 2, 2011

(86) PCT No.: PCT/US2011/023502
§ 371 (c)(1),
(2), (4) Date: Aug. 2, 2012

(87) PCT Pub. No.: WO2011/097315
PCT Pub. Date: Aug. 11, 2011

(65) Prior Publication Data
US 2012/0296433 A1 Nov. 22, 2012

Related U.S. Application Data

(60) Provisional application No. 61/300,580, filed on Feb. 2, 2010.

(51) Int. Cl.
*A61F 2/44* (2006.01)
*A61B 17/02* (2006.01)
*A61F 2/30* (2006.01)
*A61F 2/28* (2006.01)

(52) U.S. Cl.
CPC ............ *A61F 2/4465* (2013.01); *A61F 2/442* (2013.01); *A61B 2017/0256* (2013.01); *A61F 2/30907* (2013.01); *A61F 2002/2817* (2013.01); *A61F 2002/2835* (2013.01); *A61F 2002/3055* (2013.01); *A61F 2002/30405* (2013.01); *A61F 2002/30448* (2013.01); *A61F 2002/30484* (2013.01); *A61F 2002/30556* (2013.01); *A61F 2002/30579* (2013.01); *A61F 2002/30841* (2013.01); *A61F 2002/30914* (2013.01)

(58) Field of Classification Search
CPC ..... A61F 2/4405; A61F 2/442; A61F 2/4425; A61F 2/46; A61F 2/4611; A61F 2002/30362; A61F 2002/30405; A61F 2002/30411; A61F 2002/30484; A61F 2002/30518; A61F 2002/30537; A61F 2002/30538; A61F 2002/3054; A61F 2002/30545; A61F 2002/3055; A61F 2002/30553; A61F 2002/30555; A61F 2002/30556; A61F 2002/4495; A61F 2002/448
USPC ................ 623/17.11–17.16; 606/90
See application file for complete search history.

(56) References Cited

U.S. PATENT DOCUMENTS

| | | | | |
|---|---|---|---|---|
| 4,863,476 A | * | 9/1989 | Shepperd | 623/17.15 |
| 5,059,194 A | * | 10/1991 | Michelson | 606/90 |
| 5,554,191 A | * | 9/1996 | Lahille et al. | 623/17.11 |
| 6,110,210 A | * | 8/2000 | Norton et al. | 623/17.16 |
| 6,117,174 A | * | 9/2000 | Nolan | 623/17.11 |
| 6,190,414 B1 | * | 2/2001 | Young et al. | 623/17.15 |
| 6,197,033 B1 | * | 3/2001 | Haid et al. | 606/99 |
| 6,368,351 B1 | * | 4/2002 | Glenn et al. | 623/17.15 |

(Continued)

*Primary Examiner* — Pedro Philogene
*Assistant Examiner* — Lynnsy Summitt
(74) *Attorney, Agent, or Firm* — Seth D. Levy; Erik J. Birkeneder; Nixon Peabody LLP

(57) ABSTRACT

The invention relates to a device intended to replace or partially replace one or more vertebral bodies or intervertebral discs in the cervical, thoracic or lumbar spine, and includes methods for its use and deployment. The invention may be used to restore biomechanical parameters correlating with improved patient outcomes and also involves a method for a more effective discectomy or corpectomy prior to graft deployment.

20 Claims, 9 Drawing Sheets

(56) References Cited

U.S. PATENT DOCUMENTS

| | | | |
|---|---|---|---|
| 6,371,989 B1* | 4/2002 | Chauvin et al. | 623/17.11 |
| 6,395,031 B1* | 5/2002 | Foley et al. | 623/17.11 |
| 6,491,724 B1* | 12/2002 | Ferree | 623/17.11 |
| 6,723,128 B2* | 4/2004 | Uk | 623/17.15 |
| 6,955,691 B2* | 10/2005 | Chae et al. | 623/17.16 |
| 7,083,650 B2* | 8/2006 | Moskowitz et al. | 623/17.11 |
| 7,204,851 B2* | 4/2007 | Trieu et al. | 623/17.11 |
| 7,217,291 B2* | 5/2007 | Zucherman et al. | 623/17.15 |
| 7,217,293 B2* | 5/2007 | Branch, Jr. | 623/17.16 |
| 7,220,280 B2* | 5/2007 | Kast et al. | 623/17.11 |
| 7,618,454 B2* | 11/2009 | Bentley et al. | 623/17.11 |
| 7,621,951 B2* | 11/2009 | Glenn et al. | 623/17.11 |
| 7,621,960 B2* | 11/2009 | Boyd et al. | 623/17.16 |
| 7,655,042 B2* | 2/2010 | Foley et al. | 623/17.11 |
| 7,655,046 B2* | 2/2010 | Dryer et al. | 623/17.15 |
| 7,749,270 B2* | 7/2010 | Peterman | 623/17.11 |
| 7,854,766 B2* | 12/2010 | Moskowitz et al. | 623/17.15 |
| 7,875,079 B2* | 1/2011 | Melkent | 623/17.15 |
| 7,879,098 B1* | 2/2011 | Simmons, Jr. | 623/17.11 |
| 7,981,031 B2* | 7/2011 | Frasier et al. | 600/224 |
| H2261 H* | 8/2011 | Simmons, Jr. | 623/17.11 |
| 8,100,828 B2* | 1/2012 | Frey et al. | 600/234 |
| 8,133,173 B2* | 3/2012 | Miles et al. | 600/202 |
| 8,137,284 B2* | 3/2012 | Miles et al. | 600/554 |
| 8,137,401 B2* | 3/2012 | Stad et al. | 623/17.11 |
| 8,221,502 B2* | 7/2012 | Branch, Jr. | 623/17.15 |
| 8,241,362 B2* | 8/2012 | Voorhies | 623/17.16 |
| 8,262,738 B2* | 9/2012 | Melkent | 623/17.16 |
| 8,361,154 B2* | 1/2013 | Reo | 623/17.16 |
| 8,377,138 B2* | 2/2013 | Reo et al. | 623/17.16 |
| 8,403,990 B2* | 3/2013 | Dryer et al. | 623/17.15 |
| 8,409,282 B2* | 4/2013 | Kim | 623/17.11 |
| 8,439,832 B2* | 5/2013 | Miles et al. | 600/214 |
| 8,439,931 B2* | 5/2013 | Dinville | 606/99 |
| 8,444,697 B1* | 5/2013 | Butler et al. | 623/17.16 |
| 8,486,149 B2* | 7/2013 | Saidha et al. | 623/17.16 |
| 8,517,935 B2* | 8/2013 | Marchek et al. | 600/233 |
| 8,518,113 B2* | 8/2013 | Allard et al. | 623/17.11 |
| 8,518,120 B2* | 8/2013 | Glerum et al. | 623/17.16 |
| 8,535,353 B2* | 9/2013 | Johnson et al. | 606/279 |
| 8,550,995 B2* | 10/2013 | Frasier et al. | 600/244 |
| 8,551,173 B2* | 10/2013 | Lechmann et al. | 623/17.12 |
| 8,556,979 B2* | 10/2013 | Glerum et al. | 623/17.16 |
| 8,579,976 B2* | 11/2013 | Attia | 623/17.11 |
| 8,579,979 B2* | 11/2013 | Edie et al. | 623/17.15 |
| 8,602,984 B2* | 12/2013 | Raymond et al. | 600/219 |
| 8,613,773 B2* | 12/2013 | Barrett | 623/17.16 |
| 8,622,897 B2* | 1/2014 | Raymond et al. | 600/231 |
| 8,636,657 B2* | 1/2014 | Hamada | 600/233 |
| 8,663,329 B2* | 3/2014 | Ernst | 623/17.15 |
| 8,663,332 B1* | 3/2014 | To et al. | 623/17.16 |
| 8,672,840 B2* | 3/2014 | Miles et al. | 600/214 |
| 8,679,006 B2* | 3/2014 | Miles et al. | 600/202 |
| 8,679,183 B2* | 3/2014 | Glerum et al. | 623/17.16 |
| 8,679,184 B2* | 3/2014 | Kube, II | 623/17.16 |
| 8,685,095 B2* | 4/2014 | Miller et al. | 623/17.11 |
| 8,709,086 B2* | 4/2014 | Glerum | 623/17.16 |
| 8,747,307 B2* | 6/2014 | Miles et al. | 600/202 |
| 8,771,360 B2* | 7/2014 | Jimenez et al. | 623/17.16 |
| 2002/0026195 A1* | 2/2002 | Layne et al. | 606/72 |
| 2004/0002758 A1* | 1/2004 | Landry et al. | 623/17.11 |
| 2004/0249461 A1* | 12/2004 | Ferree | 623/17.11 |
| 2005/0060036 A1* | 3/2005 | Schultz et al. | 623/17.15 |
| 2005/0216085 A1* | 9/2005 | Michelson | 623/17.11 |
| 2005/0256576 A1* | 11/2005 | Moskowitz et al. | 623/17.12 |
| 2005/0256582 A1* | 11/2005 | Ferree | 623/17.16 |
| 2006/0041313 A1* | 2/2006 | Allard et al. | 623/17.15 |
| 2006/0129244 A1* | 6/2006 | Ensign | 623/17.16 |
| 2006/0247778 A1* | 11/2006 | Ferree et al. | 623/17.14 |
| 2007/0191951 A1* | 8/2007 | Branch | 623/17.11 |
| 2007/0198025 A1* | 8/2007 | Trieu et al. | 606/105 |
| 2007/0270875 A1* | 11/2007 | Bacher et al. | 606/90 |
| 2007/0282448 A1* | 12/2007 | Abdou | 623/17.15 |
| 2008/0161928 A1* | 7/2008 | Trieu | 623/17.16 |
| 2010/0063592 A1* | 3/2010 | Dwyer et al. | 623/17.16 |
| 2010/0070036 A1* | 3/2010 | Implicito | 623/17.16 |
| 2011/0035011 A1* | 2/2011 | Cain | 623/17.16 |
| 2011/0130838 A1* | 6/2011 | Morgenstern Lopez | 623/17.16 |
| 2011/0172774 A1* | 7/2011 | Varela | 623/17.16 |
| 2011/0288646 A1* | 11/2011 | Moskowitz et al. | 623/17.16 |
| 2012/0158145 A1* | 6/2012 | Ralph et al. | 623/17.16 |
| 2012/0185049 A1* | 7/2012 | Varela | 623/17.16 |
| 2012/0203347 A1* | 8/2012 | Glerum et al. | 623/17.16 |
| 2012/0226357 A1* | 9/2012 | Varela | 623/17.16 |
| 2012/0310348 A1* | 12/2012 | Pafford et al. | 623/17.16 |
| 2013/0085572 A1* | 4/2013 | Glerum et al. | 623/17.16 |
| 2013/0150971 A1* | 6/2013 | DeFalco et al. | 623/17.16 |
| 2013/0274882 A1* | 10/2013 | Guizzardi et al. | 623/17.16 |
| 2014/0025169 A1* | 1/2014 | Lechmann et al. | 623/17.16 |
| 2014/0039622 A1* | 2/2014 | Glerum et al. | 623/17.15 |
| 2014/0052253 A1* | 2/2014 | Perloff et al. | 623/17.15 |
| 2014/0052254 A1* | 2/2014 | Glerum et al. | 623/17.15 |
| 2014/0058516 A1* | 2/2014 | Glerum et al. | 623/17.16 |
| 2014/0058519 A1* | 2/2014 | Glerum et al. | 623/17.16 |
| 2014/0094916 A1* | 4/2014 | Glerum et al. | 623/17.15 |
| 2014/0121774 A1* | 5/2014 | Glerum et al. | 623/17.16 |
| 2014/0128977 A1* | 5/2014 | Glerum et al. | 623/17.16 |
| 2014/0180421 A1* | 6/2014 | Glerum et al. | 623/17.16 |

* cited by examiner

0°

5°

10°

15°

SPINE SURGERY DEVICE

CROSS-REFERENCE TO RELATED APPLICATIONS

This application is the National Phase of International Application PCT/US11/23502, filed Feb. 2, 2011, which designated the U.S. and that International Application was published under PCT Article 21(2) in English. This application also includes a claim of priority under 35 U.S.C. §119(e) to U.S. provisional patent application No. 61/300,580, filed Feb. 2, 2010.

BACKGROUND OF THE INVENTION

1. Field of the Invention

The present invention is directed generally to a device intended to replace or partially replace a vertebral body or intervertebral disc in the cervical, thoracic or lumbar spine, as well as methods for its use and deployment.

2. Description of the Related Art

All publications cited herein are incorporated by reference in their entirety to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Various devices are known in the art for the replacement or partial replacement of vertebral bodies or intervertebral discs in the cervical, thoracic, and lumbar spine. These are often used to replace, restore, correct, augment, strengthen, support or maintain height of an unstable, fractured, collapsed, damaged, degenerated or degraded vertebral body segment or intervertebral disc space or portion thereof, which has compromised integrity due to cancer or tumor or other lesion including hematalogic, metabolic or other systemic processes affecting spinal structures; is unstable because of trauma or any other process compromising integrity of ligaments, soft tissues, or osseous structures; or is characterized by a degenerative or deforming process including but not limited to congenital deformities, degenerative disease, kyphosis, spinal deformity/scoliosis, or spondylolisthesis. The device described herein is also relevant and applicable as it pertains to any spinal segment that has a surgical indication based on patient presentation and surgeon's judgment with no limitations otherwise. Cervical neck pain or axial back pain with or without radicular symptoms are frequently symptoms, and neurologic deficit involving loss of strength or sensation is frequently a sign, of such conditions. Further devices and methods are known in the art for performing the surgical procedures required to effectuate the removal of disc tissue or osseous structures and achieve the insertion and placement of some type of spinal segment replacement device.

The number of thoracic and lumbar fusions being performed has increased dramatically during the past ten years, far in excess of what would be expected proportionately considering population growth and aging demographics alone. Spine surgeons are now seeing many patients return post-fusion with symptoms limiting their professional, personal, and social functionality that stem from a fusion performed in the past without appropriate consideration for the biomechanical principle of sagittal balance and restoration of lumbar lordosis. The vast majority of thoracic and lumbar fusions are currently performed through a posterior approach, through a posterolateral fusion that does not involve interbody grafting or via a posterior lumbar interbody fusion ("PLIF") cage (i.e., the disc space is accessed bilaterally and extensive nerve root retraction is required) or through a transforaminal lumbar interbody fusion ("TLIF") with a TLIF cage (i.e., the spine is approached posteriorly similar to the PLIF, but unilaterally more from the side of the spinal canal through the foramen, potentially reducing nerve root retraction required to access the disc). The traditional posterior approach is well-tolerated by patients but can restrict the amount of disc material that can be removed safely and more importantly restricts the size and type of currently available cage that can be placed through this small opening, an orifice limited by the degree of traction that can be placed on critical nerve roots or otherwise limited by the window of access to the disc space. Current grafts available for insertion via a posterior approach are hampered by subphysiologic degrees of lordosis and endplate coverage, compared with anatomically appropriate lordotic grafts with larger endplate coverage. Given currently available technology, marketed grafts and described techniques, these subpar grafts are inserted from a posterior trajectory and do not restore appropriate lumbar lordosis or sagittal balance. Up to now, limited space afforded by a posterior approach because of proximity of critical nerve roots has seemingly and supposedly limited the size and type of graft that has been marketed as available for posterior insertion. Insertion of a smaller and biomechanically misproportioned graft, as necessitated by current grafts that are available for insertion from a posterior approach at this time, may lead to a higher rate of pseudoarthrosis and lower rate of fusion, since surface area contact of endplate vs. graft is less than that obtained during an anterior approach where a larger and more biomechanically appropriate graft can be implanted. Anatomically and biomechanically, the posterior approach to discectomy and fusion, using currently available implants, is further limited in its ability to reestablish optimal lumbar lordosis and restore global sagittal balance (global sagittal imbalance is defined as a distance of greater than 50 mm from the C7 sagittal vertical axis and the S1 sagittal vertical axis), key biomechanical phenomena proven in the literature to be critical to successful patient outcomes. See, e.g., S D Glassman et al., "The impact of positive sagittal balance in adult spinal deformity," *Spine* 30(18):2024-9 (2005).

Although the posterior approach to the spine can be faster, easier and less risky in most patients, many surgeons find that the anterior approach to the spine and placement of an Anterior Lumbar Interbody Fusion ("ALIF") cage is more advantageous because of larger endplate coverage and increased degree of lordosis of the graft that can be implanted, thus achieving greater graft-endplate surface area contact and better biomechanical establishment of lumbar lordosis and restoration of sagittal balance. This procedure is performed from the ventral aspect of the spine, usually through a 3-5 inch incision in the lower left abdominal area. This incision may involve cutting through, and later repairing, the muscles in the lower abdomen, retracting the peritoneum, and retracting the great vessels and ureter. This enables total direct discectomy and placement of a large lordotic cage with generous endplate contact, resulting in excellent fusion rates, and superb reestablishment of lumbar lordosis and sagittal balance. However, the ALIF is somewhat limited in its employment because it requires access to the anterior part of the spine to be provided by a trained vascular or other qualified surgeon before the spine surgeon can perform discectomy and fusion (whereas the posterior approach does not require an approach surgeon). The anterior approach can lead to life-threatening consequences, such as loss of limb and life-threatening hemorrhage, as well as retrograde ejaculation in men, impairing their fertility. The anterior approach may also require further posterior stabilization subsequently, thus leaving patients with an incision from the front of the abdomen and a second incision from the back. Finally, the anterior approach carries a risk of abdominal pseudohernia or true hernia. These potential complications and hassles explain why most spine surgeons prefer the more practical posterior approach and use currently available grafts, but compromise with fusion rates, lordosis reestablishment and sagittal balance correction that is inferior to an anterior approach with a more biomechanically sound graft.

The ideal then would be a graft that can be inserted from a posterior approach (which carries the least risk of morbidity for the patient) but achieves similar benefits to grafts currently available for anterior insertion in terms of restoring sagittal balance and lumbar lordosis. While there are some devices known in the art that are configured for posterior insertion while seeking increased disc and intervertebral height in excess of that traditionally achieved by grafts used in the past during the posterior approach, these devices each suffer from their own limitations and do not correct for the biomechanical shortcomings of current grafts as described above.

There thus remains a need in the art for a device that is configured substantially for posterior insertion (but that can indeed be inserted from an anterior or lateral trajectory as well), and that incorporates the superior biomechanical advantages of an ALIF-type deployment device (e.g., restoring anatomic degree of lumbar lordosis and sagittal balance and improving graft-endplate contact in order to improve fusion rates), while obviating various physiological, mechanical and practical challenges of placement that would otherwise accompany placement from an anterior trajectory. The graft should be placed after thorough and extensive discectomy with minimal risk of harming critical neurovascular structures by way of a protected portal. Described herein is a device and method that simultaneously accomplishes the above.

SUMMARY OF THE INVENTION

In an embodiment, the invention includes an apparatus, comprising: a first element having a top and a bottom; a second element having a top and a bottom; one or more bridging structures, each in mechanical communication with both the first element and the second element, wherein upon actuation of the one or more bridging structures, the first element and the second element separate from one another; and a lordotic expander, wherein upon actuation of the lordotic expander, the top and the bottom of the first element expand apart from one another. The one or more bridging structures may each comprise complementary male and female screw threading. The apparatus may be generally bullet-shaped. The lordotic expander may be configured to be actuated by a series of rotational clicks. Each of said rotational clicks may represent an approximately 5° increase in lordosis when said apparatus is inserted and deployed in an intervertebral space. The first element may be configured to be placed in the posterior region of an intervertebral space following its deployment in a spine surgery procedure. The second element may be configured to be placed in the anterior region of an intervertebral space following its deployment in a spine surgery procedure. The top of the first element and/or the top of the second element and/or the bottom of the first element and/or the bottom of the second element may independently comprise a surface treatment to reduce migration following insertion and deployment of the apparatus in an intervertebral space. The surface treatment may comprise spikes, teeth or an adhesive. The apparatus may be configured to mechanically communicate with a tool, whereby actuation of the tool causes actuation of the one or more bridging structures. The apparatus may be configured to mechanically communicate with a tool, whereby actuation of the tool causes actuation of the lordotic expander. The apparatus may be adapted for insertion into an intervertebral space through a handle of a distractor tool.

In another embodiment, the invention includes, in combination, the aforementioned apparatus and a distractor tool, the distractor tool comprising: a handle; and an expansion mechanism attached to the handle, the expansion mechanism to controllably expand or retract in both the anterior-posterior direction and the rostral-caudal direction within an intervertebral space. The expansion mechanism may further comprise a first pair of blades to controllably expand or retract in the anterior-posterior direction, and a second set of blades to controllably expand or retract in the rostral-caudal direction.

In another embodiment, the invention includes, in combination, the aforementioned apparatus and a mesh structure to contain a quantity of a material, a graft material or a fusion-promoting chemical or protein. The mesh structure may be incorporated within a space created between the first element and the second element following insertion and deployment of the apparatus. The apparatus may be encapsulated within the mesh structure.

In another embodiment, the invention includes a method, comprising: providing an apparatus, comprising: a first element having a top and a bottom, a second element having a top and a bottom, one or more bridging structures, each in mechanical communication with both the first element and the second element, wherein upon actuation of the one or more bridging structures, the first element and the second element separate from one another, and a lordotic expander, wherein upon actuation of the lordotic expander, the top and the bottom of the first element expand apart from one another; inserting the apparatus into an intervertebral space; actuating the one or more bridging structures; and actuating the lordotic expander. Prior to inserting the apparatus into the intervertebral space, the method may further comprise removing an intervertebral disc, debris, soft tissues or osseous structures from the intervertebral space. Inserting the apparatus into the intervertebral space may further comprise: providing a distractor tool comprising a handle and an expansion mechanism attached to the handle, the expansion mechanism to controllably expand or retract in both the anterior-posterior direction and the rostral-caudal direction within an intervertebral space; expanding the expansion mechanism; and repositioning the apparatus through the handle and into the intervertebral space.

BRIEF DESCRIPTION OF THE SEVERAL VIEWS OF THE DRAWING(S)

Exemplary embodiments are illustrated in referenced figures. It is intended that the embodiments and figures disclosed herein are to be considered illustrative rather than restrictive.

FIG. 4(A)-(D) depicts a cross-sectional view of an internal mechanism for lordotic expansion of a device, in accordance with an embodiment of the present invention.

Figure 5:
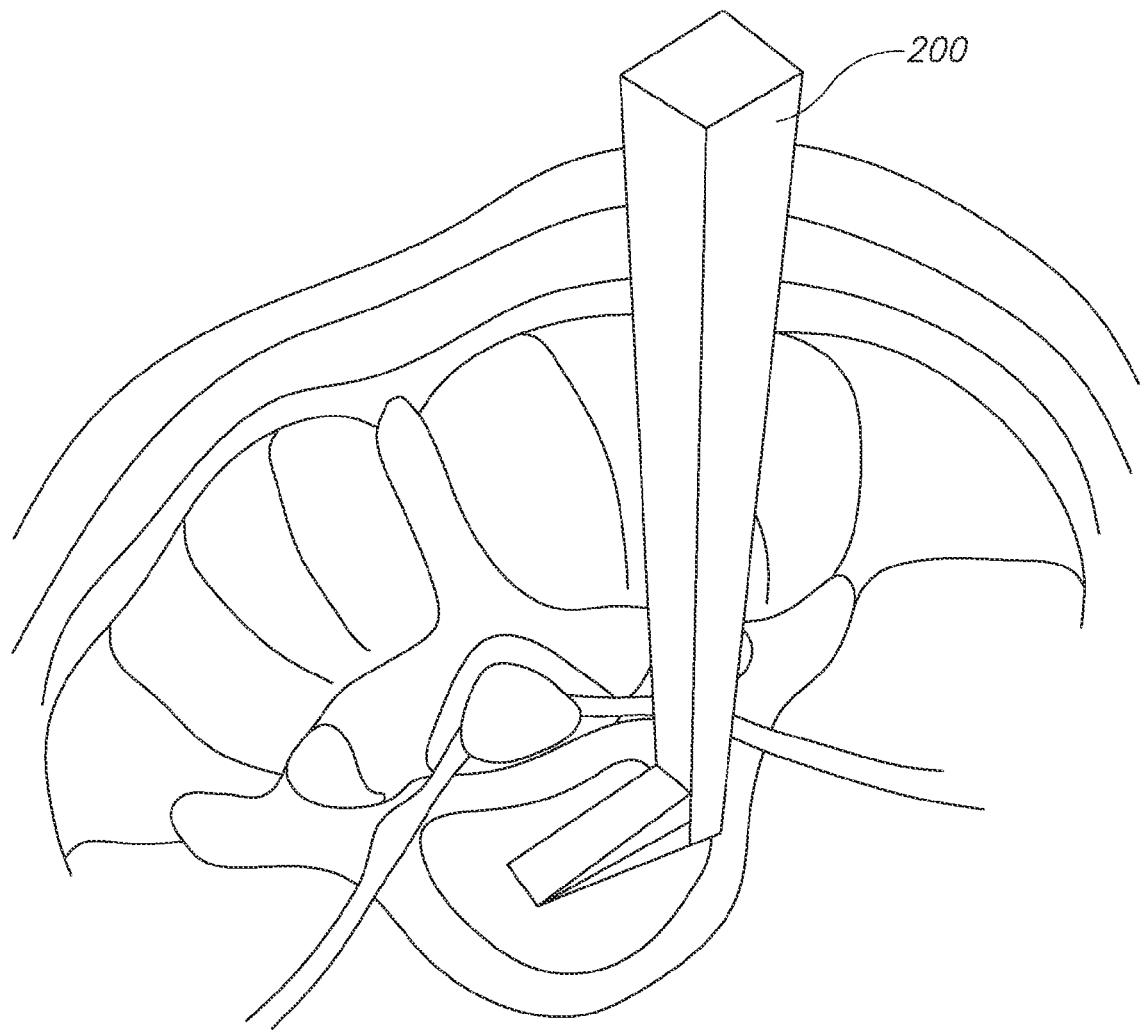

FIG. 5 depicts insertion of a distractor tool, in accordance with an embodiment of the present invention.

Figure 6B:
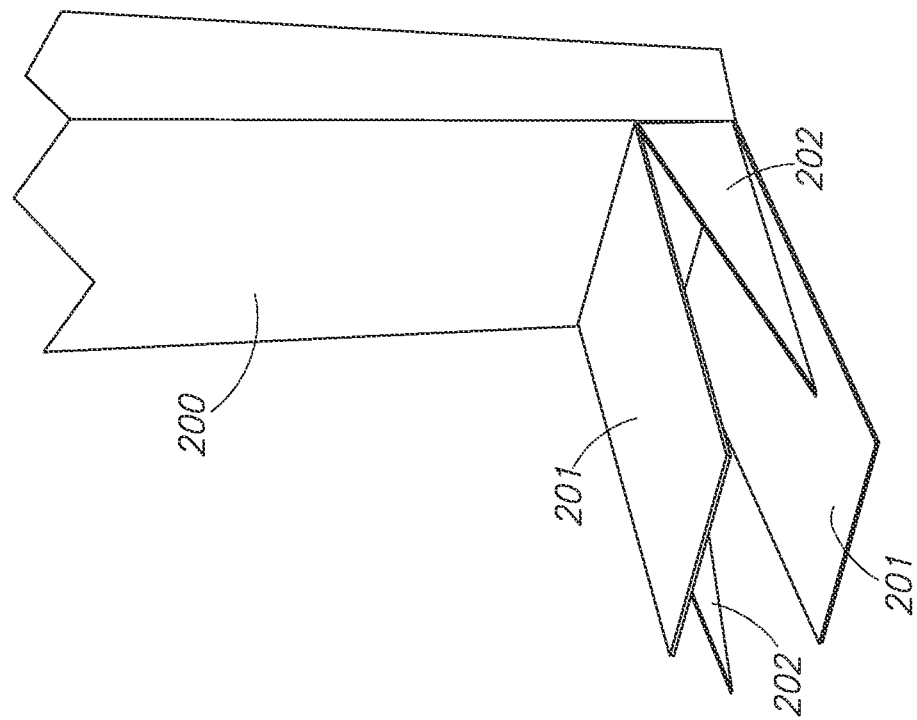
Figure 6A:
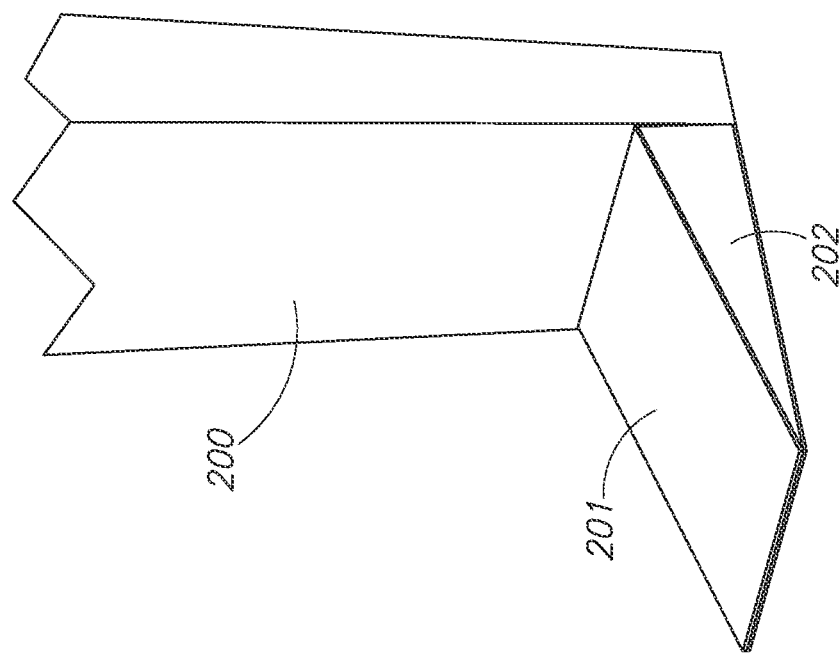
Figure 7A:
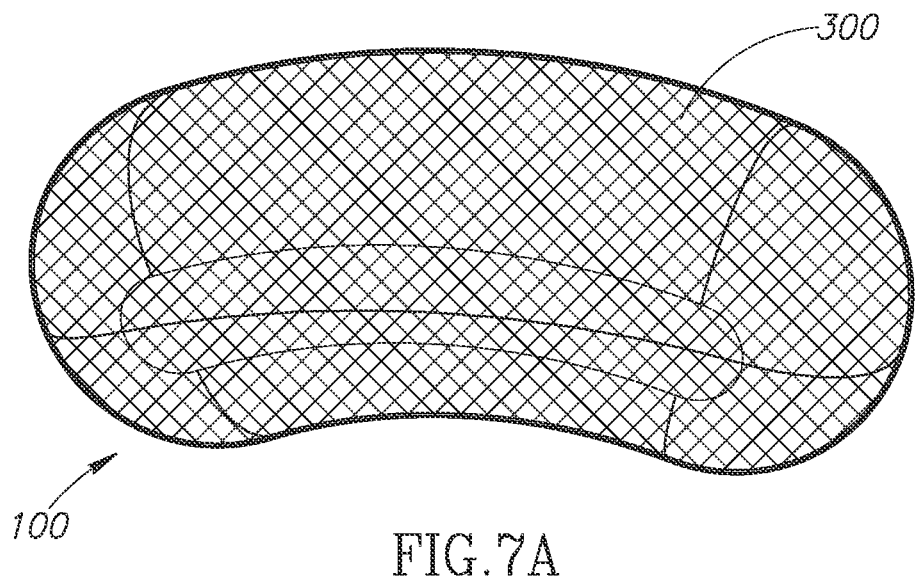
Figure 7B:
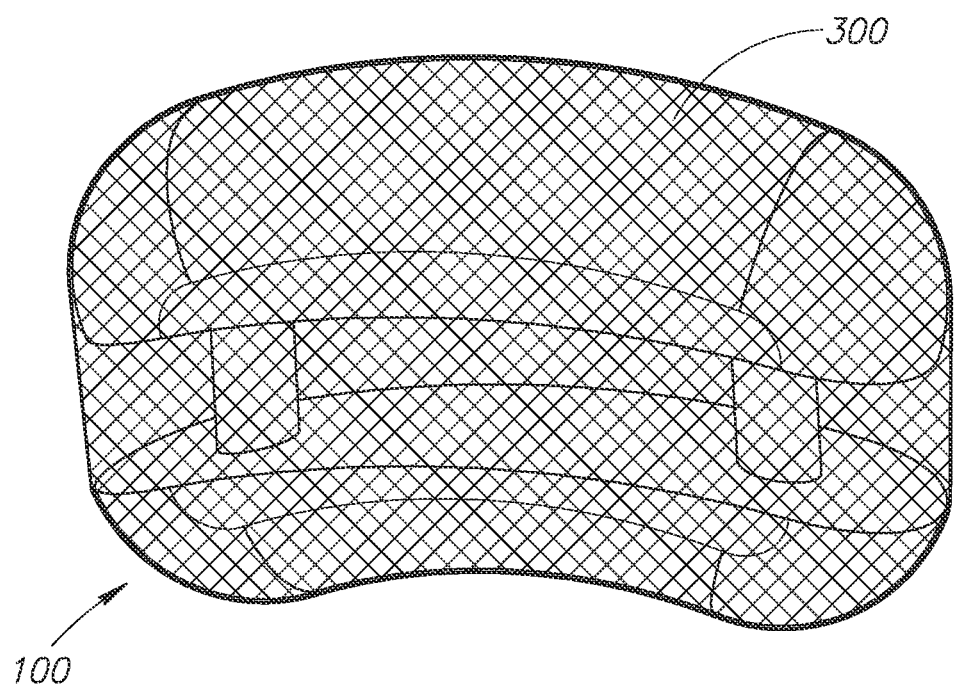
Figure 7C:
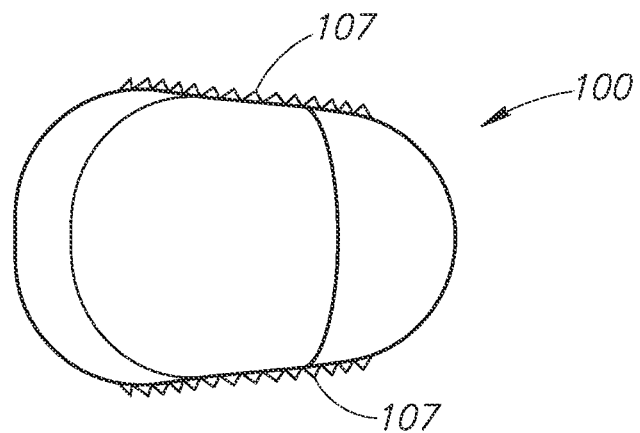
Figure 7D:
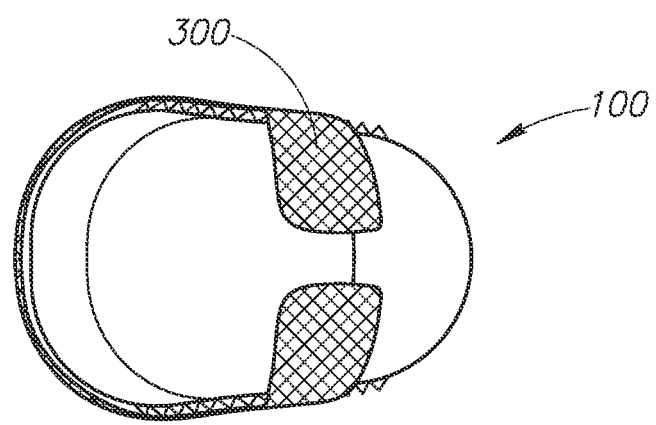
Figure 7E:
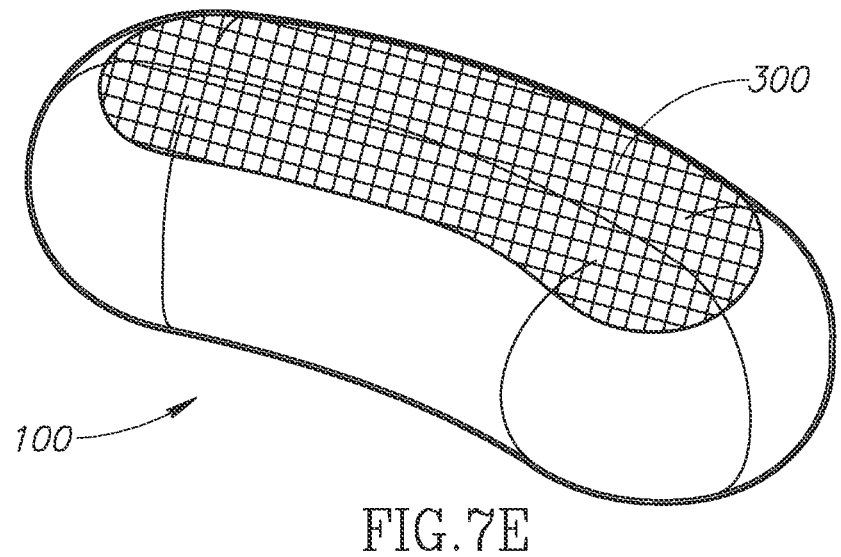
Figure 7F:
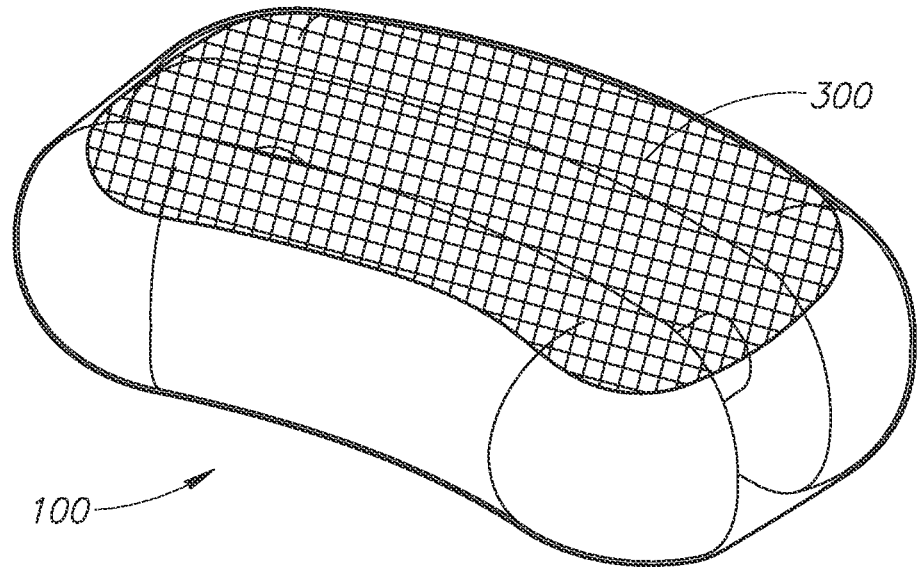

FIG. 6 depicts the deployment end of a distractor tool in (A) closed and (B) open positions, in accordance with an embodiment of the present invention.

FIG. 7 depicts a perspective view of a mesh structure encapsulating a device in (A) pre-deployment top view and (B) post-deployment configurations, top view after anterior-posterior expansion, (C) a sagittal or side perspective view of a device with spikes after anterior-posterior and lordotic deployment, (D) a mesh structure attached to a device with the same deployment as in (C), and a mesh structure configured atop a device in top views (E) pre-anterior-posterior deployment and (F) post-anterior-posterior deployment configurations, each in accordance with various embodiments of the present invention.

Figure 8:
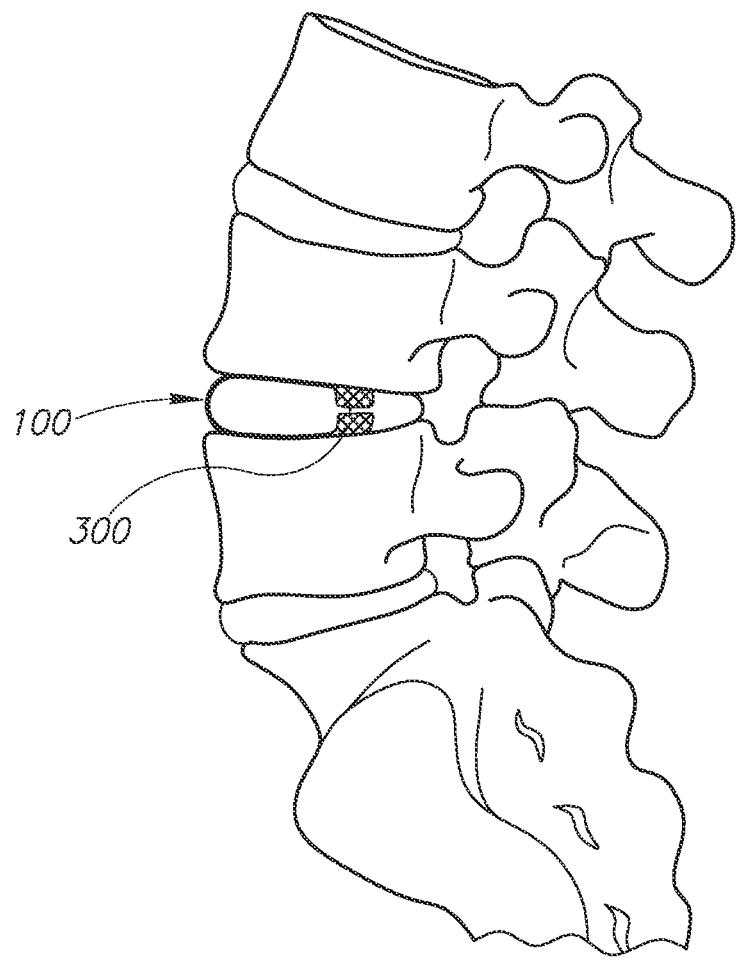

FIG. 8 depicts a side or sagittal, perspective view of a device, post-anterior-posterior and lordotic deployment and with a mesh structure attached to it, expanded post-deployment in an intervertebral space, in accordance with an embodiment of the present invention.

DETAILED DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. One skilled in the art will recognize many methods and materials similar or equivalent to those described herein, which could be used in the practice of the present invention. Indeed, the present invention is in no way limited to the methods and materials described.

The invention relates to a device intended to replace or partially replace one or more vertebral bodies or intervertebral discs in the cervical, thoracic or lumbar spine. The device is configured to be inserted through a posterior approach and may require a spine surgeon only, thereby obviating the need for an anterior approach and its associated complications. Several additional features of the device set it apart from other cages inserted through a posterior approach; for instance, and among other things, it may be introduced through a unique posterior insertion technique allowing for an extensive discectomy through a protected portal that safeguards the neural elements posteriorly and vascular elements anteriorly; the device may eventually expand to approximate the size of an ALIF cage with superior endplate contact and fusion rate; and the device may enable reestablishment of lumbar lordosis from 0 to 15 degrees or other various degrees and can help reestablish global sagittal balance. The device can be inserted through a traditional small posterior approach to the disc space or vertebral body that accommodates the initial pre-deployment compact size of the cage, which is then expandable not only in rostral-caudal height/degrees of lordosis anteriorly, but also expandable in the anterior-posterior direction. These features are illustrated in the accompanying drawings, and are currently not commercially available through other cages and similar devices.

Figure 1:
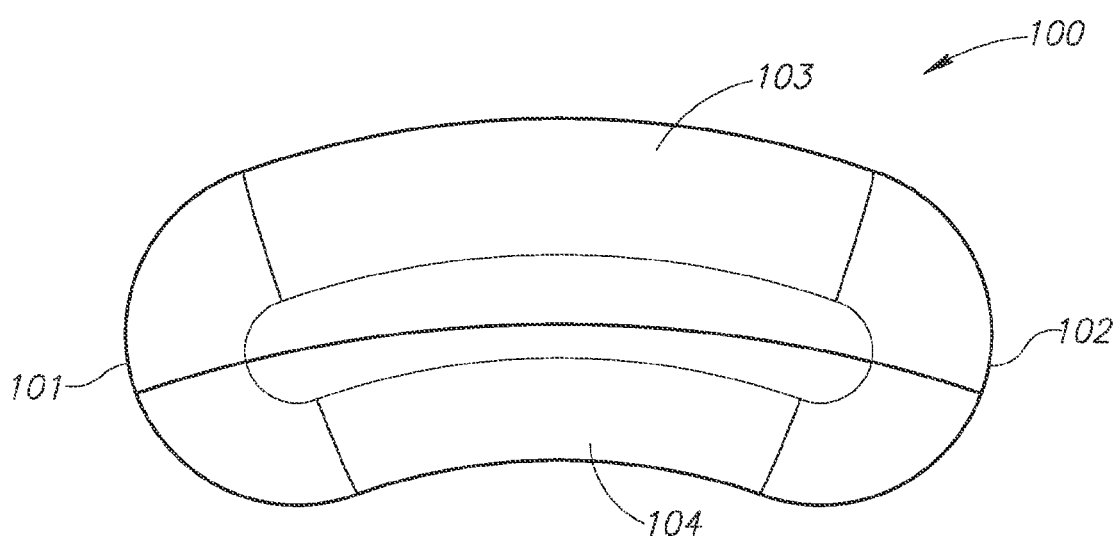
FIG. 1 depicts a top view of a device in a closed position (e.g., prior to surgical insertion), in accordance with an embodiment of the present invention.
Figure 2:
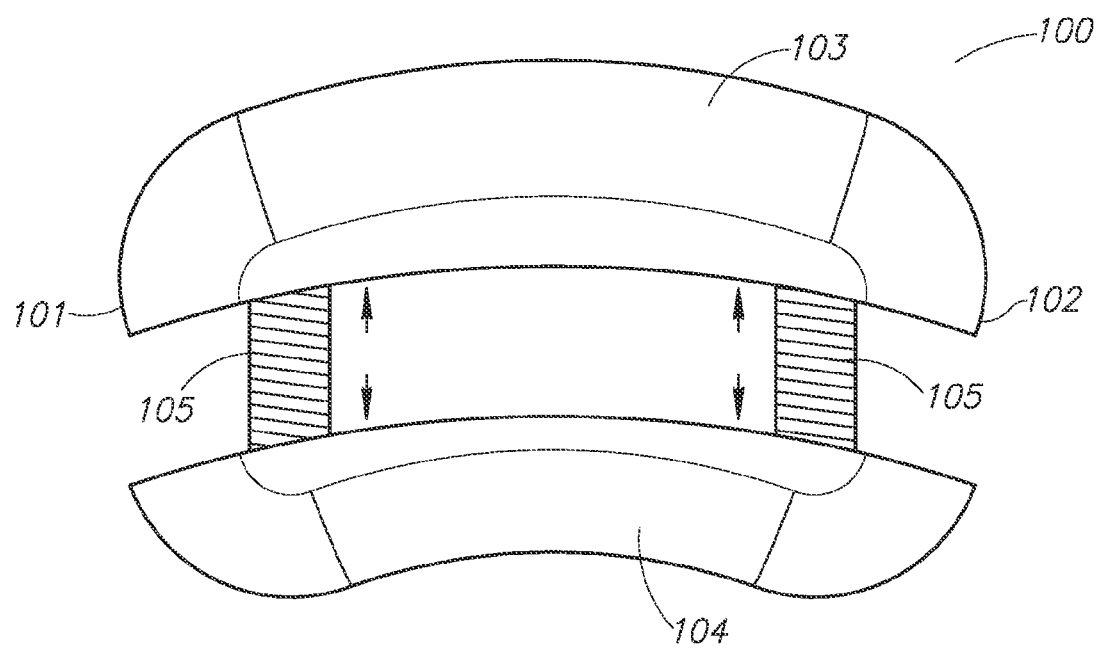
FIG. 2 depicts a top view of a device that has been expanded in the anterior-posterior direction (arrows illustrate direction of anterior-posterior expansion), in accordance with an embodiment of the present invention.
Figure 3:
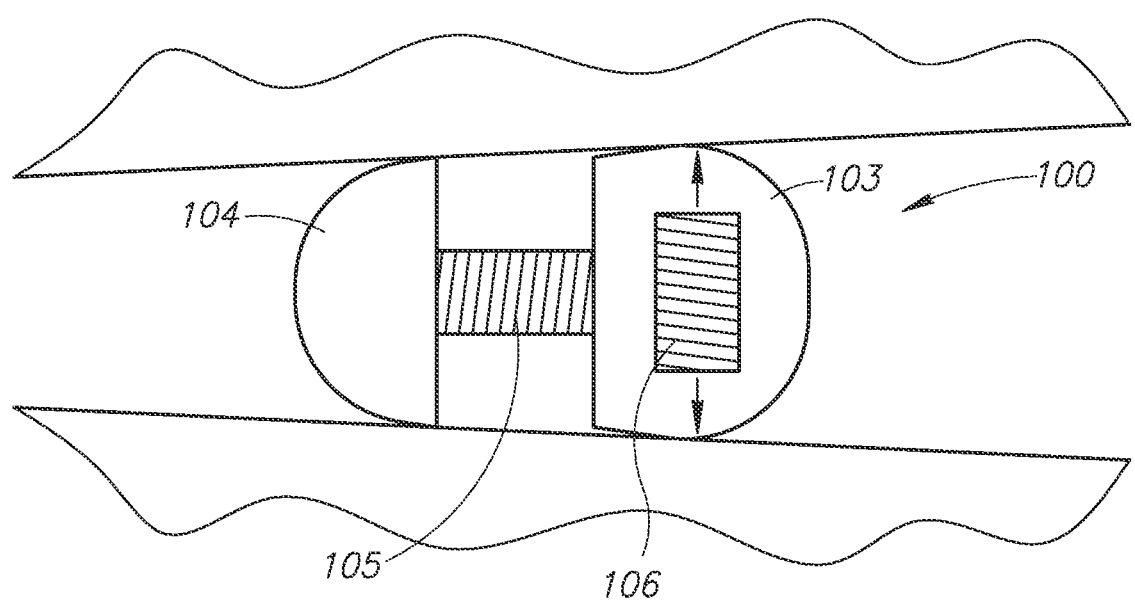
FIG. 3 depicts a sagittal, cross-sectional view of a device that has been expanded in the anterior-posterior direction and wherein arrows depict lordotic expansion, in accordance with an embodiment of the present invention.
Figure 4A:
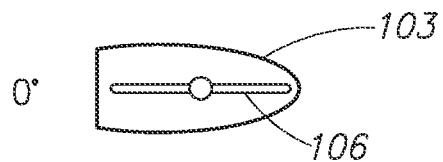
Figure 4B:
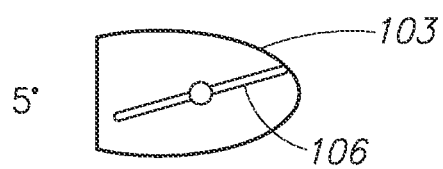
Figure 4C:
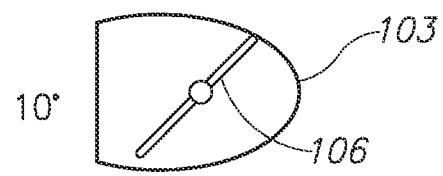
Figure 4D:
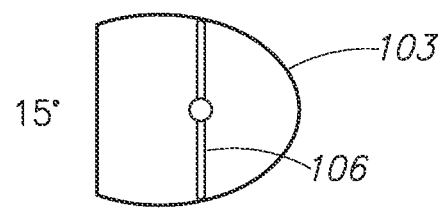

In one embodiment, the device 100 is illustrated in FIGS. 1-3, which depict a top view of the device in compact form prior to in situ deployment (FIG. 1), a top view of the device following in situ deployment and anterior-posterior expansion (FIG. 2), and a sagittal cross-sectional view of the device following both in situ deployment, anterior and posterior expansion and lordotic expansion (FIG. 3). The device 100 is intended for the replacement or partial replacement of a collapsed, degenerated, damaged or unstable vertebral body or intervertebral disc or portion thereof.

The device 100 may be generally bullet-shaped at one or both of its ends 101, 102 (the device 100 illustratively depicted in the Figures is bullet-shaped at both ends). This may aid in insertion of the device 100 into the interbody space, which may follow partial or total discectomy or corpectomy or other substantial clearing of tissue, debris and/or other material from the interbody space. The device 100 may incorporate two elements that are connected; a first element 103 that is configured to remain in the anterior region of the interbody space following insertion and deployment, and a second element 104 that is configured to remain in the posterior region of the interbody space following insertion and deployment. As used herein, "deployment" refers to the mechanical process by which the first element 103 and second element 104 are distracted from one another into their desired locations but still connected via bridging structures 105 to each other, and "lordotic expansion" refers to the mechanical process by which the first element 103 is expanded in the rostral-caudal direction so as to impart the desired angle of lordosis to that segment of the spine.

Anterior-posterior deployment and lordotic expansion of the device 100 may each be effectuated by actuation of a single or more tools that are adapted to mechanically interact with the device 100 to achieve each of these results. In each case, the tool(s) can be controlled by the surgeon. This may be accomplished, for instance, through actuation of a mechanical or electronic mechanism on or in communication with the tool(s) to create the desired result. In the case of deployment, actuation of the tool(s) causes the first element 103 and second element 104 to separate from one another to either a single predetermined distance or a distance that may be controlled by the surgeon depending on a variety of factors that will be appreciated by those of skill in the art (e.g., configuration and structure of the disc space, bone quality of endplate, extent of discectomy, etc.). Separation of the first element 103 and the second element 104 from one another is illustratively depicted in FIG. 2.

One or more bridging structures 105 may cause deployment by operating to drive the first element 103 and the second element 104 away from one another through use of the aforementioned tool(s). The bridging structures 105 may comprise any number of mechanical components to achieve this desired function, as will be readily apparent to those of skill in the art. Simply by way of example, the bridging structures 105 may include complementary male and female screw threading, such that the rotation of particular elements within the bridging structures 105 forces the first element 103 and second element 104 apart from one another. Alternatively, the bridging structures 105 may comprise a peg and groove system.

A lordotic expander 106 may operate to increase the overall "height" of the first element 103 in the rostral-caudal direction, again, through use of the aforementioned single or multiple tools. In alternate embodiments (not shown), a second lordotic expander that operates either together with or independently of the lordotic expander 106 in the first element 103 may be included in the second element 104. As illustrated in FIG. 4, the lordotic expander 106 may actuate via a series of rotational "clicks," whereby each "click" further increases the height of at least a portion of the first element 103. In FIG. 4, four such settings are illustrated, whereby a final lordosis of each of 0°, 5°, 10° and 15° can be obtained (or other proscribed degrees as may be desirable). In alternate embodiments of the device 100, a greater or fewer number of options for angles of final lordotic expansion may be permitted. In any case, lordotic expansion causes the top and bottom of the second element 104 to move apart from one another by a distance of anywhere from 1 mm to as many as 15 cm, depending upon the number of vertebral bodies being replaced, the degree of lordosis sought to be achieved, or any number of other physiologic or biomechanical factors that would be readily appreciated by those of skill in the art. Thus, in various embodiments of the present invention, an expansion range for the lordotic expander 106 can be 1 mm-10 mm, 1 mm-1 cm, 10 mm-2 cm, 1 cm-6 cm, 1 cm-10 cm, 5 cm-15 cm, or any other range of expansion from as little as 1 mm on the low end to as much as 15 cm at the high end. Moreover, expansion of lordotic expander 106 may occur in a manner whereby the top and bottom surfaces remain in parallel planes relative to one another once the lordotic expander 106 has been actuated, or, in an alternate embodiment, the top and bottom surfaces do not remain in parallel planes relative to one another following actuation of the lordotic expander 106.

The surfaces of the first element 103 and second element 104 that are intended to come into contact with the vertebrae following insertion and deployment may be configured so as to reduce migration. For instance, these surfaces may include spikes, teeth or other mechanical features 107 (FIG. 7C) or they might include or be impregnated with adhesives, substrates that promote fusion to the endplate, or other biochemical elements (not shown) that prevent or at least reduce the likelihood of migration following surgery and may promote fusion once final position is accepted by the surgeon. By way of example, these might include mechanical, anatomic, morphogenic, or chemical components that promote a graft residing in a biomechanically appropriate position initially selected by a surgeon and in a manner that retards migration.

In a further embodiment of the invention, one or more expandable balloon and/or mesh structures may be included to biomechanically support the device 100 and to contain a volume of material (e.g., graft material) or other fusion-promoting chemical/protein to enhance fusion following surgery. Any number of such structures and corresponding materials are known to those of skill in the art and can be implemented in combination with the device 100 by routine procedures. By way of example, a mesh structure 300 may be incorporated within the space created between the first element 103 and second element 104 following deployment. Alternatively, the entire device 100 may be encapsulated within a mesh structure 300 (FIG. 7A, 7B), or a mesh structure 300 can be configured partially or entirely alongside, within, atop or otherwise nearby the device 100 when deployed (FIGS. 7D, 7E, 7F and 8). Depending upon the configuration, the mesh structure 300 may also expand in the manner and directions that the device 100 expands; for instance, in both the anterior-posterior direction (as may be achieved with the device 100 by actuation of the bridging structures 105) as well as the rostral-caudal direction (as may be achieved with the device 100 by actuation of the lordotic expander 106).

With regard to the tools referenced above, as illustrated in FIG. 5, one embodiment of the invention includes a distractor tool 200 configured for insertion into the interbody space. In an embodiment, the distractor tool includes a four-blade expansion mechanism 201, 202 at the end designed for introduction into the interbody space. In alternate embodiments, the expansion mechanism can have any number of geometric configurations, such as triangular, rectangular, square, rhomboidal or trapezoidal. Upon actuation of the tool, a first pair of blades 202 can controllably expand or retract in the anterior-posterior direction safely without overexpansion and can self-maintain various degrees of expansion through mechanical means while the surgeon continues to operate, thereby protecting the great vessels and neural structures respectively during discectomy. A second pair of blades 201 can controllably expand or retract in the rostral-caudal direction without violating the endplates to increase disc and foraminal height. Expansion of the distraction tool in the rostral-caudal direction may include the use of a series of sequentially larger asymmetric metal disc space dilators that can be malletted through the distractor to achieve lordotic end plate distraction without violating the end plate or a variety of other mechanical means to achieve the same. All four blades can self-retain a variable degree of expansion safely and can be guarded against overdistraction via particular mechanical mechanisms. In various embodiments of the distractor tool, the two pairs of blades 201, 202 may be operated either together or independently from one another. In various embodiments of the distractor tool, the two pairs of blades confer protection of critical surrounding neurovascular structures, including nerve roots and iliac arteries and veins, during a surgical procedure.

The distractor tool 200 may be configured to operate with a disc removal tool. The disc removal tool is adapted to remove disc (e.g., under fluoroscopic guidance) and gently decorticate bone as an option if desired given quality of the endplate to prepare a fusion bed for the device 100. In one embodiment, the disc removal tool includes a rotating shaver and a vacuum suction device, thereby allowing a surgeon to mechanically disrupt disc and related materials in the interbody space or in the intervertebral space and simultaneously remove these items from the interbody space by operation of the vacuum. In one embodiment, the disc removal tool is configured to operate in concert with the distractor tool; for instance, once the distractor tool is inserted to increase disc and foraminal height and protect neurovascular structures, the disc removal tool can be inserted and operated through the hollow neck of the distractor tool and thus reach the interbody space. In operation, the disc removal tool may have a variety of safety features, including, by way of example, a feature that results in an alarm when the disc removal tool, in operation, contacts cortical bone, so the surgeon can avoid breach of the cortex.

In yet another embodiment of the invention, the device 100 is configured to be inserted into the interbody space through the neck of the distractor tool. In another embodiment of the invention, one or more additional tools (such as an inserter tool) are configured to operate through the neck of the distractor tool to position, deploy and/or actuate various mechanical features of the device 100. For instance, an inserter tool may be used to actuate the bridging structures 105 and/or the lordotic expander 106. In one embodiment of the invention, a single tool (or possibly multiple tools) may be used for cage insertion, expanding in the anterior-posterior direction, lordotic expansion in the rostral-caudal direction, further tamping and adjusting of cage final position under fluoroscopic guidance, retraction and removal of cage, and insertion of fusion or graft material.

EXAMPLES

The following non-limiting examples are provided to further illustrate embodiments of the invention disclosed herein.

It should be appreciated by those of skill in the art that the techniques disclosed in the examples that follow represent approaches that have been found to function well in the practice of the invention, and thus can be considered to constitute an example of a mode for its practice. However, those of skill in the art should, in light of the present disclosure, appreciate that many changes can be made in the specific embodiments that are disclosed and still obtain a like or similar result without departing from the spirit and scope of the invention.

A device as illustrated in FIG. 1 is provided, along with a distractor tool as described herein and a disc removal tool as described herein. During a spine surgery procedure, following macroscopic discectomy, the distractor tool is inserted into the interbody space, and its pairs of blades are extended in the rostral-caudal and anterior-posterior directions to protect neural tissue (at the posterior region of the interbody space) and vascular structures (at the anterior region of the interbody space). The blades may be retracted back and no longer extended, as needed. The disc removal tool reaches the interbody space through the neck of the distractor tool, and is used to remove remaining disc and to potentially decorticate bone once distractor blades covering the endplates are removed in order to prepare a fusion bed. The disc removal tool is then removed.

The cage device is then inserted into the interbody space through the neck of the distractor tool with the blades of the distractor tool retracted to allow for proper placement of the cage device against the endplates, and mechanical force may be employed (e.g., through use of a mallet) to properly orient and position the device within the interbody space. Fluoroscopy may also be used to guide proper placement of the device. The device is then deployed in the anterior-posterior direction (by pushing down on a lever-handle on an inserter tool or other mechanism for deployment that is in mechanical communication with the device and its bridging structures) and lordotic expansion is achieved to the desired angle (by rotating a dial (e.g., a clicking dial) on the handle of or otherwise actuating the inserter tool to control the lordotic expander in the device) as described above. Proper placement is confirmed via fluoroscopy. If the position of the device is satisfactory, a mesh positioned around the cage is filled with graft or other fusion-promoting material, the device is then disengaged from the inserter tool (which is removed), and the distractor tool is then removed.

The various methods and techniques described above provide a number of ways to carry out the invention. This patent description pertains to any interbody device that is expandable in the anterior-posterior trajectory in situ and/or can achieve variable degrees of lordosis in situ, depending on the clinical indication. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Various embodiments of the invention can specifically include or exclude any of these variations or elements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the invention and does not pose a limitation on the scope of the invention otherwise claimed.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

The invention claimed is:

1. An apparatus, comprising:
    a first element having a top and a bottom;
    a second element having a top and a bottom;
    one or more bridging structures, each in mechanical communication with both the first element and the second element, wherein upon actuation of the one or more bridging structures, the first element and the second element separate from one another; and a lordotic expander, wherein upon actuation of the lordotic expander, the top and the bottom of the first element expand apart from one another without changing the distance between the top and bottom of the second element.

2. The apparatus of claim 1, wherein the one or more bridging structures each comprise complementary male and female screw threading.

3. The apparatus of claim 1, wherein the apparatus is generally bullet-shaped.

4. The apparatus of claim 1, wherein the lordotic expander is configured to be actuated by a series of rotational clicks.

5. The apparatus of claim 4, wherein each of said rotational clicks represents an approximately 5° increase in lordosis when said apparatus is inserted and deployed in an intervertebral space.

6. The apparatus of claim 1, wherein the top of the first element and/or the top of the second element and/or the bottom of the first element and/or the bottom of the second element independently comprise a surface treatment to reduce migration following insertion and deployment of the apparatus in an intervertebral space.

7. The apparatus of claim 6, wherein the surface treatment comprises spikes, teeth or an adhesive.

8. The apparatus of claim 1, configured to mechanically communicate with a tool, whereby actuation of the tool causes actuation of the one or more bridging structures.

9. The apparatus of claim 1, configured to mechanically communicate with a tool, whereby actuation of the tool causes actuation of the lordotic expander.

10. The apparatus of claim 1, adapted for insertion into an intervertebral space through a handle of a distractor tool.

11. In combination, the apparatus of claim 1 and a distractor tool, the distractor tool comprising:

a handle; and an expansion mechanism attached to the handle, the expansion mechanism to controllably expand or retract in both the anterior-posterior direction and the rostral-caudal direction within an intervertebral space.

12. The combination of claim 11, wherein the expansion mechanism further comprises a first pair of blades to controllably expand or retract in the anterior-posterior direction, and a second set of blades to controllably expand or retract in the rostral-caudal direction.

13. In combination, the apparatus of claim 1 and a mesh structure to contain a quantity of a material, a graft material or a fusion-promoting chemical or protein.

14. The combination of claim 13, wherein the mesh structure is incorporated within a space created between the first element and the second element following insertion and deployment of the apparatus.

15. The combination of claim 13, wherein the apparatus is encapsulated within the mesh structure.

16. The apparatus of claim 1, wherein the distance between the top and bottom of the second element is fixed.

17. The apparatus of claim 1, wherein the direction of separation of the first element from the second element after actuation of the one or more bridging structures is approximately orthogonal to the direction of expansion of the top and bottom of the first element after actuation of the lordotic expander.

18. A method, comprising:

providing an apparatus, comprising:

a first element having a top and a bottom, a second element having a top and a bottom, one or more bridging structures, each in mechanical communication with both the first element and the second element, wherein upon actuation of the one or more bridging structures, the first element and the second element separate from one another, and a lordotic expander, wherein upon actuation of the lordotic expander, the top and the bottom of the first element expand apart from one another without changing the distance between the top and bottom of the second element;

inserting the apparatus into an intervertebral space;

actuating the one or more bridging structures; and actuating the lordotic expander.

19. The method of claim 18, wherein prior to inserting the apparatus into the intervertebral space, the method further comprises removing an intervertebral disc, debris, soft tissues or osseous structures from the intervertebral space.

20. The method of claim 18, wherein inserting the apparatus into the intervertebral space further comprises:

providing a distractor tool comprising a handle and an expansion mechanism attached to the handle, the expansion mechanism to controllably expand or retract in both the anterior-posterior direction and the rostral-caudal direction within an intervertebral space;

expanding the expansion mechanism; and repositioning the apparatus through the handle and into the intervertebral space.

* * * * *